United States Patent
Davies et al.

(10) Patent No.: US 11,576,886 B2
(45) Date of Patent: Feb. 14, 2023

(54) CONSTRUCTS COMPRISING FATTY ACIDS

(71) Applicant: POLYREM LIMITED, London (GB)

(72) Inventors: Tony Davies, London (GB); Deirdre McIntosh, Ceredigion (GB); Malcolm Weetman, Surrey (GB)

(73) Assignee: Polyrem Limited, London (GB)

( * ) Notice: Subject to any disclaimer, the term of this patent is extended or adjusted under 35 U.S.C. 154(b) by 0 days.

(21) Appl. No.: 16/763,526

(22) PCT Filed: Nov. 13, 2018

(86) PCT No.: PCT/GB2018/053272
§ 371 (c)(1),
(2) Date: May 12, 2020

(87) PCT Pub. No.: WO2019/092449
PCT Pub. Date: May 16, 2019

(65) Prior Publication Data
US 2020/0323806 A1    Oct. 15, 2020

(30) Foreign Application Priority Data
Nov. 13, 2017  (GB) ..................................... 1718741

(51) Int. Cl.
| | |
|---|---|
| *A61K 31/201* | (2006.01) |
| *A61K 47/64* | (2017.01) |
| *A61K 47/52* | (2017.01) |
| *A61P 1/02* | (2006.01) |
| *A61P 25/22* | (2006.01) |
| *A61P 19/02* | (2006.01) |
| *A61P 1/00* | (2006.01) |
| *A61K 9/00* | (2006.01) |

(52) U.S. Cl.
CPC .......... *A61K 31/201* (2013.01); *A61K 9/0056* (2013.01); *A61K 47/52* (2017.08); *A61K 47/64* (2017.08); *A61P 1/00* (2018.01); *A61P 1/02* (2018.01); *A61P 19/02* (2018.01); *A61P 25/22* (2018.01)

(58) Field of Classification Search
CPC ...... A61K 31/201; A61K 47/64; A61K 47/52; A61K 9/00; A61P 25/22; A61P 1/02; A61P 19/02; A61P 1/00
See application file for complete search history.

(56) References Cited

U.S. PATENT DOCUMENTS

| | | | |
|---|---|---|---|
| 9,034,385 B2 * | 5/2015 | Lorenzon | A23K 40/35 424/490 |
| 2005/0152852 A1 | 7/2005 | Nishimura et al. | |
| 2006/0024245 A1 | 2/2006 | Gebreselassie et al. | |
| 2006/0068019 A1 | 3/2006 | Dalziel et al. | |
| 2012/0009239 A1 | 1/2012 | Porubcan et al. | |
| 2016/0029670 A1 | 2/2016 | Ito et al. | |
| 2016/0101033 A1 | 4/2016 | Finjan et al. | |
| 2017/0215457 A1 * | 8/2017 | Serino | A23K 20/10 |

FOREIGN PATENT DOCUMENTS

| | | |
|---|---|---|
| WO | WO2001095914 | 12/2001 |
| WO | WO2007122624 | 11/2007 |
| WO | WO2013096596 | 6/2013 |
| WO | WO 2017042094 | * 3/2017 |

OTHER PUBLICATIONS

Alcock, et al., "Fatty Acids From Diet and Microbiota Regulate Energy Metabolism," F1000Res., 2015; 4(F1000 Faculty Rev), 738, 10 pages.
McLaughlin, et al., "Fatty acid chain length determines cholecystokinin secretion and effect on human gastric motility," Gastroenterology, vol. 116, No. 1, 1999, pp. 46-53.
Myers, et al., "Impact of palmitic acid and [alpha]-linolenic acid on the [beta]-catenin pathway with inhibition of the peroxisome proliferator-activated receptor [gamma] ( PPAR [gamma]) in HCT116 colon cancer cells," The FASEB Journal, vol. 30, No. 1, supplement, 2016, pp. 1-4.
Ohlsson, et al., "Cholecystokinin stimulation leads to increased oxytocin secretion in women," Eur. J. Surg., vol. 168, No. 2, 2002, pp. 114-118.
The IBO in Epic Study Investigators, "Linoleic acid, a dietary n-6 polyunsaturated fatty acid, and the aetiology of ulcerative colitis: a nested case-control study within a European prospective cohort study", Gut, vol. 58, No. 12, 2009, 6 pages.
Office Action dated May 3, 2021 in European Application No. 18804102.4, 5 pages.
Office Action dated Jul. 19, 2018 in Great Britain Application No. 1718741.0, 5 pages.
Shanbhag, "Oil pulling for maintaining oral hygiene—A review," J. Tradit. Complement Med., vol. 7, No. 1, 2017, pp. 106-109.

* cited by examiner

*Primary Examiner* — Shirley V Gembeh
(74) *Attorney, Agent, or Firm* — Lee & Hayes PC; C. Rachal Winger; Chrystal Quisenberry

(57) ABSTRACT

The present invention relates to a construct comprising a C13 to C27 fatty acid non-covalently bound to a hydrophobic region of a carrier particle, methods of manufacture, and uses thereof.

23 Claims, 3 Drawing Sheets

(A)

(B)

(C)

CONSTRUCTS COMPRISING FATTY ACIDS

CROSS-REFERENCE TO RELATED APPLICATIONS

This application is a US national stage entry of International Patent Application No. PCT/GB2018/053272 filed Nov. 13, 2018, which claims priority to GB Patent Application No. 1718741.0, filed Nov. 13, 2017, the entire contents of both of which are incorporated by reference herein.

The present invention relates to constructs comprising fatty acids bound to a carrier particle, and related uses thereof.

The interaction between the complex microorganism communities colonising the human and animal gastrointestinal tract (the microbiota) and their host has, in recent years, been recognised to play an important role in regulating host health and well-being. Indeed, the intestinal microbiota has been shown to play a role in metabolic, nutritional, physiological and immunological processes in the host body, with dysbiosis associated with both intestinal and extra-intestinal diseases.

Conventional approaches to modulate this interaction have been directed to changing the composition and activity of the microbiota using probiotic and prebiotic dietary supplements. Probiotics comprise live bacteria, which are ingested by a subject with the aim of promoting gastrointestinal tract colonisation by said bacteria. Prebiotics, on the other hand, are non-digestible (non-biotic) food ingredients that induce the growth or activity of beneficial populations of the host microbiota.

While not precluding the possibility that many of these products are beneficial, the evidence presented tends to be circumstantial rather than based on properly controlled scientific trials. For example, while studies have purportedly demonstrated the benefits of probiotics, the bacterial concentrations consumed are significantly higher than typically present in commercially-available food supplements. Criticisms have also been levelled at an apparent lack of clearly defined mechanisms of action by which probiotics exert their beneficial properties. Moreover, the laxity of regulations in relation to such products, once the basic issues of toxicity have been dealt with, has added to the difficulty of obtaining scientifically-verifiable data.

Therefore, there is a need for an improved means of modulating the microbiota/host subject interaction, including the composition and activity of said microbiota with a view to improving health and/or wellbeing of the subject.

The present invention solves at least one of the above-mentioned problems. In particular, the present inventors have found that a construct described herein can improve a subject's health and well-being by altering the physiological status of the subject's microbiota (e.g. gut flora including the buccal flora) or the interaction between the microbiota and subject.

Surprisingly, a construct of the invention is believed to alter this interaction by way of an effect on the microbiota and/or on the subject. For example, the construct may alter the composition of a subject's microbiota, stimulate the release of one or more chemical(s) (e.g. metabolites) from bacteria comprised in the subject's microbiota, and/or increase the permeability of a subject's gut to food and the microbiota or components thereof, such as bacterial vesicles/microvesicles. This in turn is believed to result in a number of downstream effects as described herein.

The present invention is directed to constructs comprising a C13 to C27 fatty acid non-covalently bound to a hydrophobic region of a carrier particle. Advantageously, constructs described herein are simple to make and/or relatively inexpensive and/or non-toxic. Indeed, the constructs may comprise constituents (e.g. wherein the carrier particle is a silica carrier particle) that have separately been approved by the European Union and United States Food and Drug Administration for oral ingestion in humans.

A fatty acid for use in the present invention may be obtainable from any source, and may be natural or synthetic. In one embodiment a fatty acid is obtainable from a plant or an animal source, in other words the fatty acid may be a plant or animal fatty acid.

The fatty acid is preferably from a plant, for example a vegetable, nut, or seed of a plant. The fatty acid is preferably obtainable from an oil of a plant.

In one embodiment the fatty acid is a rapeseed, coconut, cottonseed, castor oil, corn, olive, palm, peanut, safflower, sesame, soybean, sunflower, almond, beech nut, brazil nut, cashew, hazelnut, macadamia, mongongo nut, pecan, pine nut, pistachio, walnut, pumpkin seed, flaxseed, cocoa, or hemp fatty acid. In a particularly preferred embodiment the fatty acid is a rapeseed fatty acid.

The term "obtainable" as used herein encompasses the term "obtained". In one embodiment "obtainable" means "obtained".

Fatty acids comprise (or consist of) a carboxylic acid group attached to an aliphatic chain (e.g. an alkyl chain). A specified number of carbon atoms ($C_n$) used herein refers to the number of carbon atoms present in both the aliphatic chain and the carboxylic acid group of a fatty acid. For example, a C13 fatty acid contains 12 carbon atoms in the aliphatic chain and 1 carbon atom in the carboxylic acid group.

A fatty acid aliphatic chain may comprise (or consist of) one or more carbon-carbon double bonds ("unsaturated" fatty acids). Fatty acids having an aliphatic chain with one carbon-carbon double bond are referred to herein as "monounsaturated" fatty acids, while fatty acids having an aliphatic chain with two or more (preferably two) carbon-carbon double bonds are referred to herein as "polyunsaturated" fatty acids.

A carbon-carbon double bond may be in a cis or trans configuration. In one embodiment a fatty acid comprises (or consists of) a carbon-carbon double bond in a cis configuration. In one embodiment a fatty acid comprises (or consists of) a carbon-carbon double bond in a trans configuration. In some embodiments a fatty acid comprises (or consists of) a carbon-carbon double bond in a cis configuration and a carbon-carbon double bond in a trans configuration.

Alternatively a fatty acid aliphatic chain may have no carbon-carbon double bonds, such fatty acids are referred to herein as "saturated" fatty acids.

In one embodiment a construct described herein comprises a saturated fatty acid. Preferably, a construct described herein comprises an unsaturated fatty acid. In one embodiment a construct described herein comprises a saturated fatty acid and an unsaturated fatty acid. In one embodiment an unsaturated fatty acid is monounsaturated. In another embodiment an unsaturated fatty acid is polyunsaturated.

In one embodiment a fatty acid comprises (or consists of) at least 13, 14, 15, 16, 17, 18, 19, 20, 21, 22, 23, 24, 25 or 26 carbon atoms. In one embodiment a fatty acid comprises (or consists of) less than 27, 26, 25, 24, 23, 22, 21, 20, 19, 18, 17, 16, 15 or 14 carbon atoms. A fatty acid may comprise (or consist of) 14 to 26 carbon atoms. Preferably a fatty acid comprises (or consists of) 16 to 19 carbon atoms, for example 16 to 18 carbon atoms.

A fatty acid may be one or more selected from the following:

| Classification | | $C_n$ | Common Name | Structure |
|---|---|---|---|---|
| Unsaturated Fatty Acids | Long-Chain Fatty Acids (LCFAs) | 16 | Palmitoleic acid | $CH_3(CH_2)_5CH=CH(CH_2)_7COOH$ |
| | | 18 | Linoleic acid | $CH_3(CH_2)_4CH=CHCH_2CH=CH(CH_2)_7COOH$ |
| | | 18 | α-Linolenic acid | $CH_3CH_2CH=CHCH_2CH=CHCH_2CH=CH(CH_2)_7COOH$ |
| | | 18 | γ-Linolenic acid | $CH_3(CH_2)_4CH=CHCH_2CH=CHCH_2CH=CH(CH_2)_4COOH$ |
| | | 18 | Stearidonic acid | $CH_3CH_2CH=CHCH_2CH=CHCH_2CH=CHCH_2CH=CH(CH_2)_4COOH$ |
| | | 18 | Vaccenic acid | $CH_3(CH_2)_5CH=CH(CH_2)_9COOH$ |
| | | 18 | Oleic acid | $CH_3(CH_2)_7CH=CH(CH_2)_7COOH$ |
| | | 18 | Elaidic acid | $CH_3(CH_2)_7CH=CH(CH_2)_7COOH$ |
| | | 20 | Eicosapentaenoic acid | $CH_3CH_2CH=CHCH_2CH=CHCH_2CH=CHCH_2CH=CHCH_2CH=CH(CH_2)_3COOH$ |
| | | 20 | Dihomo-γ-linolenic acid | $CH_3(CH_2)_4CH=CHCH_2CH=CHCH_2CH=CH(CH_2)_6COOH$ |
| | | 20 | Arachidonic acid | $CH_3(CH_2)_4CH=CHCH_2CH=CHCH_2CH=CHCH_2CH=CH(CH_2)_3COOH$ |
| | | 20 | Paullinic acid | $CH_3(CH_2)_5CH=CH(CH_2)_{11}COOH$ |
| | | 20 | Gondoic acid | $CH_3(CH_2)_7CH=CH(CH_2)_9COOH$ |
| | | 20 | Mead acid | $CH_3(CH_2)_7CH=CHCH_2CH=CHCH_2CH=CH(CH_2)_3COOH$ |
| | | 22 | Docosahexaenoic acid | $CH_3CH_2CH=CHCH_2CH=CHCH_2CH=CHCH_2CH=CHCH_2CH=CHCH_2CH=CH(CH_2)_2COOH$ |
| | | 22 | Docosatetraenoic acid | $CH_3(CH_2)_4CH=CHCH_2CH=CHCH_2CH=CHCH_2CH=CH(CH_2)_5COOH$ |
| | | 22 | Erucic acid | $CH_3(CH_2)_7CH=CH(CH_2)_{11}COOH$ |
| | Very Long-Chain Fatty Acids (VLCFAs) | 24 | Nervonic acid | $CH_3(CH_2)_7CH=CH(CH_2)_{13}COOH$ |
| Saturated Fatty Acids | Medium-Chain Fatty Acids (MCFA) | 13 | Tridecylic acid | $CH_3(CH_2)_{11}COOH$ |
| | Long-Chain Fatty Acids (LCFAs) | 14 | Myristic acid | $CH_3(CH_2)_{12}COOH$ |
| | | 15 | Pentadecylic acid | $CH_3(CH_2)_{13}COOH$ |
| | | 16 | Palmitic acid | $CH_3(CH_2)_{14}COOH$ |
| | | 17 | Margaric acid | $CH_3(CH_2)_{15}COOH$ |
| | | 18 | Stearic acid | $CH_3(CH_2)_{16}COOH$ |
| | | 19 | Nonadecylic acid | $CH_3(CH_2)_{17}COOH$ |
| | | 20 | Arachidic acid | $CH_3(CH_2)_{18}COOH$ |
| | | 21 | Heneicosylic acid | $CH_3(CH_2)_{19}COOH$ |
| | | 22 | Behenic acid | $CH_3(CH_2)_{20}COOH$ |
| | Very Long-Chain Fatty Acids (VLCFAs) | 23 | Tricosylic acid | $CH_3(CH_2)_{21}COOH$ |
| | | 24 | Lignoceric acid | $CH_3(CH_2)_{22}COOH$ |
| | | 25 | Pentacosylic acid | $CH_3(CH_2)_{23}COOH$ |
| | | 26 | Cerotic acid | $CH_3(CH_2)_{24}COOH$ |
| | | 27 | Heptacosylic acid | $CH_3(CH_2)_{25}COOH$ |

In one embodiment a construct comprises a saturated MCFA, LCFA or VLCFA (preferably LCFA) selected from the table presented above. Preferably a construct comprises an unsaturated MCFA, LCFA or VLCFA (preferably LCFA) selected from the table presented above. In one embodiment a construct comprises a saturated MCFA, LCFA or VLCFA and an unsaturated MCFA, LCFA or VLCFA, more preferably a saturated LCFA and an unsaturated LCFA, selected from the table presented above.

In one embodiment a construct comprises one or more fatty acid selected from the group consisting of: margaric acid, linoleic acid, α-linolenic acid, γ-linolenic acid, stearidonic acid, vaccenic acid, oleic acid, elaidic acid, stearic acid, and nonadecylic acid. In another embodiment a construct comprises one or more fatty acid selected from the list consisting of: linoleic acid, α-linolenic acid, γ-linolenic acid, stearidonic acid, vaccenic acid, oleic acid, elaidic acid, and stearic acid. Suitably a construct may comprise one or more fatty acid selected from the list consisting of: linoleic acid, α-linolenic acid, and γ-linolenic acid.

In particularly preferred embodiment the construct comprises (or consists of) linoleic acid and oleic acid non-covalently bound to a hydrophobic region of a carrier particle.

In one embodiment a construct comprises linoleic acid, palmitic acid, stearic acid, oleic acid, and/or linolenic acid (e.g. α-linolenic acid or γ-linolenic acid). Preferably a construct comprises linoleic acid, palmitic acid, stearic acid, oleic acid, and linolenic acid (e.g. α-linolenic acid or γ-linolenic acid).

About 10-30% (preferably about 20-25%) of the total fatty acids non-covalently bound to a construct of the invention may be linoleic acid. Suitably, about 22% of the total fatty acid may be linoleic acid.

About 1-10% (preferably about 2-7%) of the total fatty acids non-covalently bound to a construct of the invention may be palmitic acid. Suitably, about 4% of the total fatty acid may be palmitic acid.

About 0.1-5% (preferably about 0.5-4%) of the total fatty acids non-covalently bound to a construct of the invention may be stearic acid. Suitably, about 2% of the total fatty acid may be stearic acid.

About 40-80% (preferably about 55-65%) of the total fatty acids non-covalently bound to a construct of the invention may be oleic acid. Suitably, about 62% of the total fatty acid may be oleic acid.

About 1-20% (preferably about 5-15%) of the total fatty acids non-covalently bound to a construct of the invention may be linolenic acid. Suitably, about 10% of the total fatty acid may be linolenic acid.

Thus, in one aspect the invention provides a construct comprising linoleic acid, palmitic acid, stearic acid, oleic acid and/or linolenic acid (e.g. α-linolenic acid or γ-linolenic acid) non-covalently bound to a hydrophobic region of a carrier particle. Also provided in one aspect is a construct described herein for use in treating an inflammatory disease. Corresponding methods of treating an inflammatory disease are also provided, the methods comprising administering said construct to a subject.

Preferably a construct of the invention comprises at least linoleic acid.

The constructs described herein preferably do not comprise a glycerol backbone. Additionally or alternatively, said constructs preferably do not comprise glycolipids, triglycerides, phospholipids or neutral lipids (e.g. comprising a glycerol backbone).

The term "non-covalently bound" as used herein refers to an interaction between two molecules that is not reliant on sharing of electrons between atoms of the two molecules. Preferably a non-covalent interaction is a hydrophobic interaction. Without wishing to be bound by theory, a hydrophobic interaction is believed to arise from the "hydrophobic effect", which relies on the energetically-favourable aggregation of non-polar molecules to avoid aqueous solution. The hydrophobic effect results in ordering of non-polar molecules (such as fatty acids) so that minimal surface area is exposed to water molecules. A shell of water molecules is believed to be involved in the hydrophobic bond thus preventing access to the hydrophobic molecules by free water molecules.

In one embodiment the term "bound" means immobilised. In one embodiment the non-covalent binding is irreversible (or substantially irreversible) under physiological conditions, meaning that when a construct of the invention has been administered to a subject (e.g. orally) the fatty acid (or a substantial concentration thereof, e.g. at least 90%, 95% or 99% of the total fatty acids per construct) remains non-covalently bound to the carrier particle.

In one embodiment the carrier particle does not bind to the carboxylic acid group of the fatty acids. In other words, the carrier particle may non-covalently bind to the aliphatic chain of a fatty acid (e.g. to a terminal portion of the aliphatic chain).

The carrier particles described herein comprise a hydrophobic region (e.g. a hydrophobic surface region), to which the fatty acids bind. At least a part of the hydrophobic region is exposed to allow interaction between the fatty acid and carrier particle. For example, at least 1%, 5%, 10%, 20%, 30%, 40%, 50%, 60%, 70% 80%, 90%, 95% or 100% of the exposed surface of the carrier particle may be hydrophobic. Preferably at least 70% or 80% of the exposed surface of the carrier particle is hydrophobic. More preferably at least 90% or 100% of the exposed surface of the carrier particle is hydrophobic.

The carrier particle may be a biological molecule. For example, the carrier particle may be a protein with one or more surface-exposed hydrophobic amino acid residues. In one embodiment said protein may be albumin. Suitably said albumin may be from an animal. In embodiments where the carrier particle is a protein, preferably said protein is not denatured.

The carrier particle is preferably a non-biological molecule, such as a silicon-containing carrier particle. For example, the carrier particle may be a silica particle, kaolin particle or vermiculite particle. Preferably the carrier particle is a silica particle, for example a pharmaceutical grade silica particle.

In one embodiment the carrier particle is non-biodegradable. In another embodiment the construct in its entirety is non-biodegradable. For example, it is preferred that the carrier particle is not a polysaccharide carrier particle and/or that the construct of the invention does not comprise a polysaccharide. In one embodiment the carrier does not comprise a starch, such as an unmodified (e.g. natural) starch or a modified starch, for example an oxidised starch, esterified starch, cross linked starch, etherified starch, carboxymethylated starch, enzymatically modified starch, hydrolysed starch, and heat treated starch.

In one embodiment the only pharmaceutically-active ingredient present in/on a construct of the invention is a fatty acid described herein.

The carrier particle may have an average diameter of at least about 2.0 or 4.0 µm. In one embodiment a carrier particle has an average diameter of at least about 6.0 or 8.0 µm.

The carrier particle may have an average diameter of less than about 1.0 µm (and optionally greater than 25 nm). Suitably a carrier particle may have an average diameter of at least about 200 nm or 400 nm.

In a particularly preferred embodiment, a carrier particle has an average diameter of greater than 500 nm. For example, a carrier particle may have an average diameter of greater than 600 nm or 700 nm. More preferably a carrier particle has an average diameter of greater than 800 nm or 900 nm.

In one embodiment a carrier particle has an average diameter of about 0.2 µm to about 20.0 µm, such as an average diameter of about 0.5 µm to about 10.0 µm. A carrier particle may have an average diameter of about 2.0 µm to about 10.0 µm, suitably about 2.0 µm to about 6.0 µm. In one embodiment a carrier particle has an average diameter of between about 2.0 µm to about 4.0 µm, suitably about 3.0 µm to about 4.0 µm. Preferably a carrier particle has an average diameter of about 3.5 µm.

In one embodiment a carrier particle is a silica particle with an average diameter of at least about 2.0 or 4.0 µm. In one embodiment the silica particle has an average diameter of at least about 6.0 or 8.0 µm.

The silica particle may have an average diameter of less than about 1.0 µm (and optionally greater than 25 nm). Suitably a silica particle may have an average diameter of at least about 200 nm or 400 nm.

In a particularly preferred embodiment, a silica particle has an average diameter of greater than 500 nm. For example, a silica particle may have an average diameter of greater than 600 nm or 700 nm. More preferably a silica particle has an average diameter of greater than 800 nm or 900 nm.

In one embodiment a carrier particle is a silica particle with an average diameter of about 0.2 µm to about 20.0 µm, such as an average diameter of about 0.5 µm to about 10.0 µm. The silica particle may have an average diameter of about 2.0 µm to about 10.0 µm, suitably about 2.0 µm to about 6.0 µm. In one embodiment the silica particle has an average diameter of between about 2.0 µm to about 4.0 µm, suitably about 3.0 µm to about 4.0 µm. Preferably the silica particle has an average diameter of about 3.5 µm.

In one embodiment the invention provides a construct comprising a C13 to C27 fatty acid non-covalently bound to a hydrophobic region of a carrier particle, wherein the average diameter of the carrier particle is greater than 0.5 µm. Preferably the average diameter of the carrier particle is at least 1.0 µm.

In one embodiment the invention provides a construct comprising at least linoleic acid, palmitic acid, stearic acid, oleic acid and/or linolenic acid non-covalently bound to a hydrophobic region of a carrier particle, wherein the average diameter of the carrier particle is greater than 0.5 µm. Preferably the average diameter of the carrier particle is at least 1.0 µm.

In one embodiment the invention provides a construct comprising a C13 to C27 fatty acid non-covalently bound to a hydrophobic region of a non-biological carrier particle, wherein the average diameter of the carrier particle is greater than 0.5 µm. Preferably the average diameter of the carrier particle is at least 1.0 µm.

In one embodiment the invention provides a construct comprising at least linoleic acid, palmitic acid, stearic acid, oleic acid and/or linolenic acid non-covalently bound to a hydrophobic region of a non-biological carrier particle, wherein the average diameter of the carrier particle is greater than 0.5 µm. Preferably the average diameter of the carrier particle is at least 1.0 µm.

In one embodiment the invention provides a construct comprising a C13 to C27 fatty acid non-covalently bound to a hydrophobic region of a silica carrier particle, wherein the average diameter of the carrier particle is greater than 0.5 µm. Preferably the average diameter of the carrier particle is at least 1.0 µm.

In one embodiment the invention provides a construct comprising at least linoleic acid, palmitic acid, stearic acid, oleic acid and/or linolenic acid non-covalently bound to a hydrophobic region of a silica carrier particle, wherein the average diameter of the carrier particle is greater than 0.5 µm. Preferably the average diameter of the carrier particle is at least 1.0 µm.

The constructs of the invention are preferably uniform particles of similar (or identical) average size. Suitably said particles may be discrete or substantially discrete (e.g. not aggregated) when in an aqueous suspension.

A construct described herein may be administered to a subject by any route suitable to achieve the desired effect. In one embodiment a construct described herein is administered orally, topically (e.g. to the buccal cavity or a component thereof, such as the teeth or gums) or rectally. Preferably, a construct described herein is orally administered to a subject.

When orally administered the construct (or a part thereof) is preferably not absorbed from a subject's gastrointestinal tract during gastrointestinal transit. For example, the construct may not cross the mucosal layer of the gastrointestinal tract of a subject orally-administered said construct. In other words, the construct (or a part thereof) described herein may be ingested, transported through a subject's gastrointestinal tract, and excreted by said subject, suitably in the faeces of said subject. In one embodiment the construct is unchanged or substantially unchanged during ingestion, transport, and excretion with a fatty acid remaining non-covalently bound to the carrier particle. Thus in one embodiment the construct is not digestible by a subject administered said construct.

The construct of the invention finds utility when administered to any triploblast. The term "triploblast" is used herein to refer to any organism having a body embryonically derived from three germ layers: the endoderm, mesoderm, and ectoderm. The triploblast further has a gut microbiota. Therefore, the term "subject" as used herein encompasses any triploblast.

In one embodiment the "subject" may be a human or non-human (e.g. animal) subject. A non-human may refer to livestock, aquatic animals (such as fish), or domesticated animals, such as pets. In one embodiment the term "subject" refers to a mammal.

In one embodiment a subject is one or more of a human, an equine species (e.g. *Equus ferus caballus*, or *Equus asinus*—donkeys), a canine species (e.g. *Canis lupus familiaris*), a bovine species (e.g. a *Bos taurus*), a porcine species (e.g. *Sus scrofa domestica*), an ovine species, a caprine species (e.g. *Capra aegagrus hircus*), a feline species (e.g. *Felis silvestris catus*), poultry (e.g. *Gallus gallus domesticus*), a fish, a rodent such as a rat, rabbit, hare, and/or mouse, and/or a camelid (such as a llama, alpaca or a camel).

In a particularly preferred embodiment a subject is a human.

In other embodiments a subject is preferably an equine (e.g. a horse).

In one embodiment a subject is a chicken, such as a broiler.

In one embodiment a subject is not a chicken, turkey or goose. Preferably the subject is not a poultry subject.

In one embodiment the subject is an insect. Suitably, an insect may be of the superfamily Apoidea. In one embodiment the insect may be selected from one or more of the following families: Andrenidae, Apidae, Colletidae, Halictidae, Megachilidae, Meganomiidae, Melittidae, Stenotritidae, and Dasypodaidae. In one embodiment the insect may be one selected from the *Apis* genus, such as one or more of the following species: *Apis mellifera, Apis lithothermaea, Apis andreniformis, Apis florea, Apis dorsata, Apis cerana, Apis koschevnikovi*, and *Apis nigrocincta*.

The construct described herein finds utility in a number of different applications.

In one aspect a construct described herein finds utility in modulating (e.g. stimulating) an endocrine system of a subject administered said construct.

In one aspect a construct described herein modulates (e.g. stimulates) neuroendocrine activity of a subject administered the construct. The modulation of neuroendocrine activity may occur by way of the hypothalamus-pituitary-adrenal (HPA) axis, as described herein.

In one embodiment the term "modulation" as used herein may refer to upregulation (i.e. stimulation) or downregulation (i.e. inhibition). Suitably, the modulation may be upregulation.

Without wishing to be bound by theory, the present inventors believe that modulation of the neuroendocrine activity allows for the treatment of one or more disorders selected from: oestrus-associated behaviour of a female subject, an oral disorder (e.g. a periodontal disorder), an ear disorder (e.g. otorrhea or ceruminosis), a gastrointestinal disorder, laminitis (e.g. seasonal laminitis), a microbial infection, an inflammatory disorder (e.g. an inflammatory intestinal disorder), a skin disorder (e.g. dermatitis, such as seborrheic dermatitis), a neurological or neurodegenerative disorder (e.g. multiple sclerosis), chronic fatigue syndrome, onychosis (i.e. a nail disorder), and a mental disorder (e.g. anxiety). Alternatively or additionally, the treatment of one or more of the above-mentioned disorders may be achieved by way of a prebiotic effect of the construct described herein (e.g. by modulating a subject's microbiota as described herein).

Thus, in one aspect the present invention provides a construct described herein for use in treating one or more disorders selected from: oestrus-associated behaviour of a female subject, an oral disorder (e.g. a periodontal disorder), an ear disorder (e.g. otorrhea or ceruminosis), a gastrointestinal disorder, laminitis (e.g. seasonal laminitis), a microbial infection, an inflammatory disorder (e.g. an inflammatory intestinal disorder), a skin disorder (e.g. dermatitis, such as seborrheic dermatitis), a neurological or neurodegenerative disorder (e.g. multiple sclerosis), chronic fatigue syndrome, onychosis (i.e. a nail disorder), and a mental disorder (e.g. anxiety).

Corresponding methods of treating one or more disorders selected from: oestrus-associated behaviour of a female subject, an oral disorder (e.g. a periodontal disorder), an ear disorder (e.g. otorrhea or ceruminosis), a gastrointestinal disorder, laminitis (e.g. seasonal laminitis), a microbial infection, an inflammatory disorder (e.g. an inflammatory intestinal disorder), a skin disorder (e.g. dermatitis, such as seborrheic dermatitis), a neurological or neurodegenerative disorder (e.g. multiple sclerosis), chronic fatigue syndrome, onychosis (i.e. a nail disorder), and a mental disorder (e.g. anxiety) comprising administering a construct described herein to a subject are also provided.

Likewise, the invention provides the use of a construct described herein in the manufacture of a medicament for treating one or more disorders selected from: oestrus-associated behaviour of a female subject, an oral disorder (e.g. a periodontal disorder), an ear disorder (e.g. otorrhea or ceruminosis [waxy ears]), a gastrointestinal disorder, laminitis (e.g. seasonal laminitis), a microbial infection, an inflammatory disorder (e.g. an inflammatory intestinal disorder), a skin disorder (e.g. dermatitis, such as seborrheic dermatitis), a neurological or neurodegenerative disorder (e.g. multiple sclerosis), chronic fatigue syndrome, onychosis (i.e. a nail disorder), and a mental disorder (e.g. anxiety).

In one embodiment the disorder is one or more selected from: an oral disorder (e.g. a periodontal disorder), an ear disorder (e.g. otorrhea or ceruminosis), and a gastrointestinal disorder. Preferably the disorder is one or more selected from: a periodontal disorder, ceruminosis, and a gastrointestinal disorder.

In a preferred embodiment the disorder is an oral disorder.

In a preferred embodiment the disorder is an ear disorder. Ear disorders may include ceruminosis (ear wax build-up) and otorrhea (ear discharge).

In another preferred embodiment the disorder is laminitis, which is a disease affecting the feet of ungulates, and its typical clinical manifestations include foot tenderness, inability to walk, increased digital pulses, and increased hoof temperature. Laminitis may be nutrition-induced, infection-induced or pressure-induced. Preferably the construct treats infection-induced laminitis (consistent with the antimicrobial activity of the construct described herein). The onset of laminitis may also be seasonal. Laminitis may also have an endocrine basis, for example secondary laminitis may be caused by an endocrinopathy.

In another preferred embodiment the disorder is a gastrointestinal disorder (e.g. an inflammatory gastrointestinal disorder). Gastrointestinal disorders treated by a construct of the invention may include irritable bowel syndrome, constipation, colic, enteritis (e.g. acute or chronic enteritis or catarrhal enteritis), acute or chronic diarrhoea, and/or coccidiosis.

In one embodiment a gastrointestinal disorder treated by the constructs described herein is constipation. Advantageously, the constructs are believed to increase gut motility, thus providing an effective treatment for the relief of constipation. Without wishing to be bound by theory, this is believed (at least in part) to be based on the anxiolytic properties of the constructs, which reduce anxiety/stress and thus reduce the associated inhibition of peristalsis.

In one aspect there is provided a construct described herein for use in treating irritable bowel syndrome. Also provided is a corresponding method for treating irritable bowel syndrome comprising administering said construct to a subject.

In another preferred embodiment the disorder is a microbial infection. Without wishing to be bound by theory, it is believed that the construct of the invention may (directly or indirectly, e.g. by way of its neuroendocrine modulation activity and/or modulation of the immune response of a subject) have antimicrobial activity, thus inhibiting/reducing microbial growth or killing microbes. Infections treated by a construct of the invention may include bacterial, eukaryotic (e.g. fungal), or viral infections. In one embodiment the infection is a bacterial infection, such as one caused by bacteria from the genus *Mycoplasma* (e.g. *Mycoplasma gallisepticum*). In another embodiment the infection is caused by a eukaryote, such as a eukaryote of the genus *Eimeria* leading to the disease of *Coccidiosis*. The microbes are preferably bacteria, more preferably pathological bacteria.

Thus, in some embodiments the construct may be used to treat a disorder caused or exacerbated by a microbial infection, which may encompass: an oral disorder (e.g. a periodontal disorder), a gastrointestinal disorder, infection-induced laminitis, an ear disorder (e.g. otorrhea), an inflammatory disorder, a skin disorder (e.g. dermatitis), and onchyosis.

The construct described herein may also improve hair shine (or coat shine for a non-human subject). Without wishing to be bound by theory it is believed that a linoleic acid component present in said construct is responsible for this effect. Surprisingly, the improvement in hair shine may be achieved by orally administering the construct to a subject.

The improvement may be determined by comparing the hair shine of the same subject before and after administration of the construct. Hair shine is preferably measured using a glossometer with or without (more preferably with) a biochemical test for the presence of linoleic acid from sebum secreted from the hair follicles. The biochemical test may measure the amount of sebum secreted, for example post-administration of the construct compared to pre-administration.

Alternatively or additionally, the hair shine measurements may include gloss analysis characteristics, which can be obtained using the SAMBA Hair system (e.g. in accordance with the manufacturer's instructions), which is commercially available from Bossa Nova Vision, 5777 W. Century Blvd, Suite 205, LA, Calif. 90045, USA. The techniques may include the use of polarization-imaging sensors to obtain specular and diffused hair images, obtaining angular profiles of specular, diffused, and chroma, and the generation of numerical data, such as luster, light intensity, shine bandwidth, etc. The following scientific publications describe techniques for measuring hair shine, and are incorporated herein by reference in their entirety: Lefaudeux N, Lechocinski N, Clemenceau P, Breugnot S. J Cosmet Sci. 2009 March-April; 60(2):153-69; Gao T, Pereira A, Zhu S., J Cosmet Sci. 2009 March-April; 60(2) 187-197; A. Jonckhéere, J. F. Tranchant, LVMH Recherche Parfums et Cosmétiques MATERIALS & SENSATIONS 2008, PAU (FRANCE), October 22-24 1; Timothy Gao, Sam Zhu, Farandia Edouard, Marni Dexter, and Jung-Mei Tien, Croda Inc., 300-A, Columbus Circle, Edison, N.J., 08837, USA, IFSCC Magazine 4-2014; TIMOTHY GAO, CHARLES MOSES, PETER LANDA, KEVIN GALLAGHER Croda Inc., 300-A, Columbus Circle, Edison, N.J., 08837, USA Monographic Supplement series: COLOUR COSMETICS Household and Personal Care today—n. 1/2012; Galliano A, Ye C, Su F, Wang C, Wang Y, Liu C, Wagle A, Guerin M, Flament F, Steel A, Int J Cosmet Sci. 2017 December; 39(6):610-616; C. J. Luptona, A. McCollb, Small Ruminant Research 99 (2011) 178-186; and Xiaosong Liu, Fumei Wang and Ian R Hardin, J Textile Sci Eng 2013, 4:1.

The construct of the invention may also modulate the immune response of a subject administered therewith. The modulation may be modulation of the adaptive or innate immune response, or a combination thereof. Modulation of said immune response may be responsible for treating one or more disorders described herein (e.g. those disorders having an immune component thereto or which are linked to (e.g. exacerbated by) an immune response in a subject).

The construct described herein may modulate activity of a subject's HPA axis.

In one aspect the present invention provides a construct for use in modulating pituitary gland activity, wherein the construct comprises a C13 to C27 fatty acid non-covalently bound to a hydrophobic region of a carrier particle. Also provided is a corresponding method for modulating pituitary gland activity comprising administering to a subject said construct.

The modulation of the pituitary gland by a construct of the invention may be stimulation or inhibition of the pituitary gland. Preferably the pituitary gland is stimulated.

The pituitary gland is part of the endocrine system and protrudes from the hypothalamus at the base of the brain. The pituitary gland secretes hormones modulating a wide variety of physiological and metabolic processes. The pituitary gland can be subdivided into three parts: the anterior pituitary which secretes at least somatotrophins, thyrotrophins, corticotrophins, lactotrophins, and gonadotropins; the intermediate pituitary which secretes at least melanocyte-stimulating hormone; and the posterior pituitary which secretes antidiuretic hormone and oxytocin. Control of hormone release from the pituitary gland (e.g. anterior pituitary) is believed to be modulated by the hypothalamus.

Pituitary modulation by a construct of the invention may arise as a result of modulation (e.g. stimulation) of a subject's hypothalamus and/or vagus nerve, which in turn modulates pituitary gland activity.

Without wishing to be bound by theory the present inventors believe that a construct of the invention alters the physiological status of a subject's microbiota (e.g. gut flora) or the interaction between the microbiota and subject. A construct of the invention is believed to alter this interaction by way of an effect on the microbiota or on the subject following administration. Thus, in one aspect there is provided a construct described herein for use in modulating a subject's microbiota, e.g. modulating an interaction between the microbiota and subject.

For example, the construct may modulate a subject's microbiota by altering the composition of a subject's microbiota, stimulating the release of one or more chemical(s) (e.g. metabolites) from bacteria comprised in the subject's microbiota, and/or increasing the permeability of a subject's gut to food and the microbiota or components thereof, such as bacterial vesicles/microvesicles. In turn it is believed that Kupffer cells in the subject's liver are stimulated to secrete cytokines. The released cytokines are believed to modulate (preferably stimulate) a subject's vagus nerve, which in turn modulates (preferably stimulates) the subject's hypothalamus, and finally modulates (preferably stimulates) the pituitary gland. Therefore the construct described herein may indirectly modulate pituitary gland activity by way of an upstream effector (e.g. the vagus nerve and/or hypothalamus, preferably the paraventricular nucleus of the hypothalamus).

Therefore in a related aspect the invention provides a construct for use in modulating activity of a subject's vagus nerve, wherein the construct comprises a C13 to C27 fatty acid non-covalently bound to a hydrophobic region of a carrier particle. Also provided is a corresponding method for modulating activity of a subject's vagus nerve, said method comprising administering to the subject said construct.

Additionally, the invention provides a construct for use in modulating activity of a subject's hypothalamus, wherein the construct comprises a C13 to C27 fatty acid non-covalently bound to a hydrophobic region of a carrier particle. Also provided is a corresponding method for modulating activity of a subject's hypothalamus, said method comprising administering to the subject said construct. Typically, the pituitary gland is responsible for storing and releasing hormones produced in the hypothalamus.

In one embodiment the paraventricular nucleus of the hypothalamus is modulated. The paraventricular nucleus (PVN) contains a group of neurones that can be activated by physiological changes. The PVN contains magnocellular neurosecretory cells (M cells) that transport the hormones oxytocin and vasopressin to the pituitary gland, where they are ultimately secreted. The PVN also contains parvocellular neurosecretory neurones that produce: corticotrophin-releasing hormone, which regulates adrenocorticotropic hormone (ACTH) secretion from the pituitary gland; vasopressin, which regulates ACTH secretion; and thyrotropin-releasing hormone, which regulates thyroid-stimulating hormone (TSH) and prolactin secretion from the pituitary gland. The PVN further contains centrally-projecting neurones (i.e. that project to other brain regions), said neurones include: parvocellular oxytocin cells that project mainly to the brainstem and spinal cord; parvocellular vasopressin cells that project to multiple locations in the hypothalamus, and limbic system, as well as the brainstem, and spinal cord; and parvocellular CRH neurones, which are believed to be involved in stress-related behaviours.

In one embodiment a construct described herein stimulates expression of the c-Fos gene leading to production the c-Fos transcription factor in the paraventricular nucleus of the hypothalamus. The c-Fos transcription factor has been implicated in modulation of numerous cellular processes, including cell proliferation, differentiation and survival. Stimulation of c-Fos production may result in downstream pituitary gland modulation.

In one aspect a construct described herein modulates (e.g. stimulates) Wnt/β-catenin signalling.

In some embodiments a construct described herein modulates (e.g. stimulates) the hypothalamic-pituitary-adrenal axis of a subject. Therefore, administration of a construct may stimulate ACTH secretion from the pituitary gland (e.g. anterior pituitary gland) of a subject. ACTH secretion may be stimulated by way of vasopressin and/or CRH produced by the hypothalamus (e.g. PVN). The secreted ACTH may stimulate the adrenal cortex to produce glucocorticoid hormones.

In one embodiment the term "modulating pituitary gland activity" as used herein refers to stimulating or inhibiting hormone release from a subject's pituitary gland. In one embodiment a hormone may be one or more selected from: somatotrophins (e.g. growth hormone), thyrotrophins (e.g. thyroid-stimulating hormone), corticotrophins (e.g. adrenocorticotropic hormone (ACTH), beta-endorphin, and melanocyte-stimulating hormone), lactotrophins (e.g. prolactin), gonadotropins (e.g. luteinizing hormone and follicle-stimulating hormone), melanocyte-stimulating hormone, antidiuretic hormone and oxytocin.

In a particularly preferred embodiment, a construct described herein stimulates secretion of oxytocin from a subject's pituitary gland. In some embodiments a construct described herein stimulates a subject's oxytocin neurones.

The term "stimulating pituitary gland activity" preferably means stimulating hormone release from a subject's pituitary gland. The term "inhibiting pituitary gland activity" preferably means inhibiting hormone release from a subject's pituitary gland.

In one aspect there is provided a construct for use in reducing/treating oestrus-associated behaviour of a female subject, wherein the construct comprises a C13 to C27 fatty acid non-covalently bound to a hydrophobic region of a carrier particle. Also provided is a corresponding method for reducing oestrus-associated behaviour of a female subject comprising administering the construct to said female subject. Suitably, a female subject may be a mammal.

In one embodiment the female subject is a human, and the oestrus-associated behaviour is premenstrual tension. Therefore, a construct of the invention may reduce/treat a symptom of premenstrual tension in a human female subject. Symptoms may include bloating, breast pain, mood swings, irritability, and/or a reduced libido.

In another embodiment the female subject is an equine species. Oestrus-associated behaviours in equines may include nickering, raising of the tail, opening/closing of the vulva (winking), vocal calling, posturing, sexual interest in other horses, anxiety, aggression, tail swishing and frequent urination. Other behaviours may include attitude changes, excessive sensitivity around the flanks, including over the region of the ovaries, and bucking and kicking when ridden. Mares exhibiting oestrus-associated behaviour may also be difficult to ride, frustrating to train and perform poorly during competitions. Advantageously, administration of a construct described herein alleviates one or more symptoms of oestrus-associated behaviour.

In other embodiments the female subject is a canine species, a bovine species, a porcine species, an ovine species, a caprine species, a feline species, a rodent species, or a camelid.

A reduction in (or treatment of) oestrus-associated behaviour may be determined using a veterinary-gauged semi-quantitative clinical scoring system. The system may be based on a scoring range of from 1-5, where:

1=normal good behaviour;
2=mildly bad behaviour;
3=moderately bad behaviour;
4=severely bad behaviour; and
5=very severe bad behaviour (e.g. with significant and often dangerous handling/management problems in the case of equines).

Bad behaviour may be characterised by a wide range of clinical signs, including squirting, kicking, biting, squealing, aggression, grumpiness, bucking, being easily spooked, anxiety, neighing when ridden, wind sucking, weaving, frequent urination, difficulty catching, tacking-up, loading and riding outside the stables, and poor performance. A lower score following treatment indicates a reduction in (or treatment of) oestrus-associated behaviour.

The present invention also provides a construct for use in treating an autoimmune disorder. Also provided is a corresponding method for treating an autoimmune disorder comprising administering said construct to a subject.

The term "disorder" as used herein also encompasses a "disease". In one embodiment the disorder is a disease.

In one embodiment the autoimmune disorder is rheumatoid arthritis.

In one aspect the invention provides a construct of the invention for use in treating an inflammatory intestinal disorder. Also provided is a corresponding method for treating an inflammatory intestinal disorder comprising administering said construct to a subject.

The inflammatory intestinal disorder may be one or more selected from: inflammatory bowel disease, ulcerative colitis, and Crohn's disease. Suitably, the inflammatory intestinal disease may be inflammatory bowel disease.

In one aspect there is provided a construct for use in treating a neurodegenerative disorder, wherein the construct comprises a C13 to C27 fatty acid non-covalently bound to a hydrophobic region of a carrier particle. Also provided is a corresponding method for treating a neurodegenerative disorder comprising administering said construct to a subject.

The constructs described herein also find utility in treating a number of other disorders (or symptoms thereof). For example, the construct may be used for the treatment of: joint or mobility disorders, demodicosis, skin disorders, neoplastic disease, respiratory disorders, gastrointestinal disorders, ear wax-related disorders (e.g. accumulation of cerumen), ocular disorders, hyperaesthesia, infection, poor weight maintenance, septic shock, hoof disorders, neoplastic disease, behavioural disorders, elevated serum glucose levels/diabetes, hypertension, and/or cancer.

Joint or mobility disorders treated by a construct of the invention may include arthritic disorders, such as osteoarthritis or adjuvant-induced arthritis.

Skin disorders treated by a construct of the invention may include dermatitis, atopy, otitis externa, feline acne, mucocutaneous pyoderma, lip fold pyoderma, nail disorders, hyperkeratosis and/or dandruff, seborrhoea sicca, sebaceous cysts, histiocytoma, mud fever, sweet itch, and/or coat conditions (including excessive hair shedding).

Respiratory disorders treated by a construct of the invention may include respiratory disease, e.g. chronic respiratory disease, and/or nasal discharge, and/or oedema.

Ocular disorders treated by a construct of the invention may include epiphora, conjunctivitis, eye discharge, and/or chronic purulent dacrocystitis.

Hoof disorders treated by a construct of the invention may include laminitis (as described above) and related disorders.

In one embodiment death rate among subjects administered a construct of the invention is reduced. In other words, survival may be improved.

A construct described herein may also improve a characteristic of a subject that is not associated with a disease or symptom thereof. Generically, the construct may improve the well-being of a subject administered therewith. In one embodiment the construct may beneficially improve growth, foodstuff utilisation, fertility, milk yield and/or quality, coat condition, lactic acid levels (e.g. reduce lactic acid levels), or combinations thereof.

Relative terms such as "improved" and "reduced" or comparative technical effects described herein are typically improved, reduced, etc. when compared to a subject that has not been administered a construct described herein (including where a subject has been administered an alternative construct or no construct at all).

In one embodiment the improvement is improved growth, such as improved growth rate.

Improved foodstuff utilisation in a subject administered a construct described herein may manifest as an improved foodstuff (e.g. feed) conversion ratio.

The improvement in fertility of a subject administered a construct described herein may be an improved fertility rate, e.g. achieved by reduced stillbirths, increased numbers of offspring or litter size, improved fertilisation/conception rates, and/or improved gamete production. In one embodiment improved fertility may be improved egg laying rate and/or size (e.g. in broiler hens).

The improvement in fertility of a subject administered a construct described herein may be an increase in the yield and/or quality of milk. In one embodiment improved milk quality is one or more of an increase in fat and/or protein content, a reduction in somatic cell count in said milk, and/or a reduced concentration of neutrophils in said milk.

In one embodiment the improvement in coat condition of a subject (e.g. non-human subject) administered a construct described herein may be an improvement in coat shine, said improvement may be visually assessed when compared to a subject that has not been administered a construct described herein (including where a subject has been administered an alternative construct or no construct at all). Alternatively or additionally said improvement may be assessed by increased sebaceous gland secretion.

Reduced lactic acid levels of a subject administered a construct described herein may advantageously reduce muscle fatigue of said subject, thus improving athletic performance.

The construct of the invention may improve/treat one or more of the disorders, symptoms or characteristics shown in the table below (e.g. enhance positive characteristics and treat negative disorders/symptoms):

| Subject | Disorder/Symptom/Characteristic Improved |
| --- | --- |
| Humans | Oestrus-associated behaviour (e.g., PMT), an oral disorder (e.g. a periodontal disorder), an ear disorder (e.g. otorrhea or ceruminosis), a gastrointestinal disorder, a microbial infection, an inflammatory disorder (e.g. an inflammatory intestinal disorder), a skin disorder (e.g. dermatitis, such as seborrheic dermatitis), a neurological or neurodegenerative disorder (e.g. multiple sclerosis), chronic fatigue syndrome, onychosis (i.e. a nail disorder), and a mental disorder (e.g. anxiety), and joint or mobility disorders |
| Dogs | Demodicosis |
| | Histiocytoma |
| | Cerumen accumulation, waxy ears |
| | Epiphora, runny eyes |
| | Chronic enteritis, persistent diarrhoea, alimentary problems |
| | Well-being |
| | Coat shine, increased sebaceous secretions |
| | Hyperkeratosis, dandruff |
| | Sebaceous cysts, skin lumps |
| | Behaviour |
| | Osteoarthritis, mobility particularly in old age |
| Cats | Hyperaesthesia, oversensitivity |
| | Hyperkeratosis, dandruff |
| | Arthritis, mobility particularly in old age |
| | Enteritis (e.g. in juvenile cats), coccidiosis |
| Rabbits | Chronic purulent dacrocystitis, eye infections |
| | Eye discharge, severe respiratory disease with nasal discharge |
| | Survival |
| Horses | Oestrus-associated behaviour |
| | Bad behaviour in mares not associated with oestrus |
| | Bad behaviour in geldings |
| | Laminitis |
| | Gastrointestinal disorders (e.g. colic) |
| | Mud fever |
| | Sweet itch |
| Domestic hens | Response to *Mycoplasma gallisepticum* infection |
| | Response to Coccidiosis (*Eimeria* spp) infection |
| | Growth rate in broilers |
| | Survival (reduced hatching weakness, trampling, growth disturbances, catarrhal enteritis and oedema of the lungs) |
| | Laying (larger more fertile eggs) |
| | Boosted vaccination response/maintenance of response |

| Subject | Disorder/Symptom/Characteristic Improved |
| --- | --- |
| Laboratory rats | Growth rate, improved feed conversion ratio<br>Adjuvant induced arthritis<br>Response to toxins |
| Pigs | Growth rate in young pigs, survival, weight gain, feed conversion ratio, immune response both adaptive and innate, response to a vaccine |
| Sheep | Milk product characteristics (e.g. quality) and growth of suckled lambs<br>Yearling lamb growth improved |
| Cattle | Milk production (reduced somatic cell count, improved milk fat and protein, increased quantity)<br>Fertility<br>Hoof conditions (equivalent to laminitis in horses) |

A construct of the invention may improve a subject's response to vaccination and/or improve maintenance of a response following vaccination. Said improved response is suitably an enhanced response to an antigen. The improved response may be measured by antibody response.

In one embodiment said construct may inhibit the cyclooxygenase enzymes COX-1 and/or COX-2. In another embodiment the construct may exhibit an anti-oxidant action in a subject administered therewith. In a further embodiment a construct described herein may reduce fat deposition in a subject. In another embodiment a construct described herein may improve survival of a subject exposed to a toxic agent. In another embodiment a construct described herein may repair imbalances between populations of T-cells in a subject administered the construct.

In one aspect there is provided a construct described herein for use in treating a mental disorder in a subject. The term "mental disorder" as used herein encompasses any mental/psychiatric disorders, including in one embodiment a mood disorder. Related methods for treating a mental disorder are also provided, said methods comprising administering a construct of the invention to a subject in need thereof. The mental disorder may be anxiety, depression (e.g. major depressive disorder), bi-polar disorder, Asperger's disease, borderline personality disorder, ADHD, bimodal reactive disorder, chronic fatigue syndrome, and autism.

The mental disorder may include behavioural disorders, such as non-oestrus associated bad behaviours.

Preferably the mental disorder is anxiety. Advantageously, the constructs of the invention may have anxiolytic properties, and therefore be suitable for treatment of anxiety. Thus, in one embodiment a construct of the invention is an anxiolytic construct. In one embodiment the subject for treatment is an equine subject, optionally where the anxiety is situational anxiety, e.g. caused by confinement and/or isolation, such as veterinary-recommended box rest.

In a related aspect a construct described herein may improve mental well-being of a subject.

A construct described herein may have a beneficial effect on the buccal flora. Therefore in one aspect there is provided a construct described herein for use in modulating a subject's buccal flora. Related methods of modulating a subject's buccal flora are also provided.

In some aspects a construct described herein is provided for use in improving oral health. In some aspects there is provided a construct described herein for use in treating an oral disorder. Associated methods of improving oral health and treating an oral disorder are also provided.

The oral disorder may be any oral disorder improved by modulating a subject's buccal flora. Thus, the oral disorder may therefore be a disorder of the buccal cavity. In a particularly preferred embodiment an oral disorder is a periodontal disorder (e.g. a gum disease), such as bleeding gums or gingivitis (e.g. chronic gingivitis).

In one embodiment an oral disorder is halitosis. Suitably, a construct described herein finds utility in reducing halitosis in a subject.

In embodiments where a construct is used for treating an oral disorder, the construct may be administered topically, e.g. to the mouth or gums. Therefore, in one aspect the present invention provides a composition formulated for application to the buccal cavity or a component thereof (such as the teeth and gums), wherein the composition comprises a construct described herein. In one embodiment the composition is a paste or mouthwash (preferably a toothpaste). In one embodiment the paste comprises (preferably consists of) the construct described herein suspended in a fatty acid composition (e.g. comprising at least linoleic acid, palmitic acid, stearic acid, oleic acid, and/or linolenic acid). The fatty acid composition may be an oil, such as a vegetable oil, preferably rapeseed oil. The fatty acid composition is preferably the same fatty acid composition that has been used to manufacture the construct. The paste suitably comprises a therapeutically or prophylactically effective amount of the construct of the invention. The composition may be used by a subject once or more than once daily. The composition will typically be used until symptoms of an oral disorder are no longer present. For example the composition may be used for up to 2 months, preferably for up to four weeks.

Advantageously, the present inventors have found that the constructs described herein improve oral health, particularly at the level of the gums. For example, a reduced periodontal pocket depth is observed in a subject after administration of the constructs when compared to the pocket depth prior to administration, thus demonstrating that the constructs improve gum health.

Pocket depth may be measured by any routine dental techniques, for example by way of a technique (such as a probing technique) described in Kim et al (2017), J Periodontal Implant Sci. 2017 February; 47(1): 13-19, Summit, James B., J. William Robbins, and Richard S. Schwartz. "Fundamentals of Operative Dentistry: A Contemporary Approach." 2nd edition. Carol Stream, Illinois, Quintessence Publishing Co, Inc, 2001. ISBN 0-86715-382-2, or Wilkins, Esther M. "Clinical Practice of the Dental Hygienist." 8th edition. Lippincott Williams & Wilkins, 1999. ISBN 0-683-30362-71, each of which is incorporated herein by reference in its entirety.

The term "treat" or "treating" as used herein encompasses prophylactic treatment (e.g. to prevent onset of a disorder) as well as corrective treatment (treatment of a subject already suffering from a disorder). Preferably "treat" or "treating" as used herein means corrective treatment. The term "treat" or "treating" encompasses treating both the disorder and a symptom thereof. In some embodiments "treat" or "treating" refers to a symptom of a disorder.

Therefore a construct of the invention may be administered to a subject in a therapeutically effective amount or a prophylactically effective amount.

A "therapeutically effective amount" is any amount of the construct, which when administered alone or in combination to a subject for treating a disorder (or a symptom thereof) is sufficient to effect such treatment of the disorder, or symptom thereof.

A "prophylactically effective amount" is any amount of the construct that, when administered alone or in combination to a subject inhibits or delays the onset or reoccurrence of a disorder (or a symptom thereof). In some embodiments, the prophylactically effective amount prevents the onset or reoccurrence of a disorder entirely. "Inhibiting" the onset means either lessening the likelihood of disorder onset (or symptom thereof), or preventing the onset entirely.

In some embodiments the construct of the invention may have a therapeutic or prophylactic effect in a subject in less than 5 or 2 hours after administration (preferably less than 1 hour after administration). It is surprising that said effect(s) are achieved so rapidly.

An appropriate dosage range is one that produces the desired therapeutic effect (e.g. wherein the construct is dosed in a therapeutically or prophylactically effective amount). Alternatively or additionally, a construct of the invention may be administered to a subject in an amount effective to improve one or more of the characteristics of a subject that is/are not associated with a disorder (or a symptom thereof).

A typical dosage regimen may comprise administering a construct of the invention once, twice, three times, four times, five times, six times or seven times per week. In one embodiment a dosage regimen comprises administering a construct of the invention daily, for example once or twice daily.

In one embodiment the construct may be dosed at at least 1, 5, 10, or 20 mg per kg bodyweight of the subject. For example, the construct may be dosed at about 1 mg to about 100 mg per kg bodyweight of the subject, suitably at about 10 mg to about 50 mg per kg bodyweight of the subject.

An appropriate dose may be about 20 mg to about 20 g of the construct daily. For example an appropriate dose may be about 45 mg to about 14 g daily, or about 100 mg to about 10 g daily. Suitably an appropriate dose may be about 500 mg to about 5 g daily, such as 1 g to about 3 g daily. These dosages may be particularly appropriate for human subjects.

In one embodiment the construct is administered at a dose of at least 1 g or 5 g daily. In another embodiment the dose is at least 10 g or 15 g daily. Suitably a dose may be at least 20 g or 25 g daily. In some embodiments up to 100 g may be dosed daily, e.g. up to 50 g daily. These dosages may be particularly appropriate for non-human subjects such as livestock (preferably equines).

In some embodiments small mammals (such as rodents) may be dosed with about 1 mg to about 30 mg per day. For example, a mouse may be dosed with about 1 mg to about 7 mg per day, while a rat may be dosed with about 10 mg to about 20 mg per day.

In some embodiments a construct of the invention may be administered to a subject in combination with one or more further therapeutic(s). Said one or more further therapeutic(s) may be administered sequentially or simultaneously with the construct of the invention.

In one embodiment a construct may be administered in combination with an anti-inflammatory therapeutic (e.g. a NSAID). In one embodiment a therapeutic may be an aminosalicylate (5-ASA), a corticosteroid, an immunomodulator, an antibiotic or a biological therapy (e.g. a therapeutic antibody). Examples of suitable therapeutics may include: prednisone, prednisolone sodium phosphate, budesonide, mesalamine, sulfasalazine, corticotropin, azathioprine, infliximab, hydrocortisone, methylprednisolone, methylprednisolone sodium succinate, mercaptopurine, dexamethasone, dexamethasone sodium phosphate, betamethasone acetate, betamethasone sodium phosphate, cyclosporine, cromolyn, mycophenolate mofetil, hydrocortisone sodium succinate, hydrocortisone acetate, triamcinolone acetonide, cortisone, methylprednisolone acetate, or combinations thereof, or pharmaceutically-acceptable salts thereof. However, advantageously, the construct described herein removes/reduces the necessity to administer an anti-inflammatory therapeutic (i.e. it is envisaged that the construct could largely replace conventional anti-inflammatory therapeutics). Surprisingly, the construct is believed to induce an anti-inflammatory response in a subject without the typical side-effects associated with conventional anti-inflammatory therapeutics (e.g. NSAIDs and/or steroids).

In some embodiments the construct described herein is administered to a subject in combination with a cancer therapeutic. Suitable cancer therapeutics are known in the art, and include for example cancer immunotherapeutics.

In one embodiment a construct of the invention may be administered with one or more probiotic(s) and/or prebiotic(s).

The invention also provides a kit comprising a construct of the invention, and instructions for use of same. The instructions may be for the use of the construct in medicine, suitably for the use of the construct to treat a disorder described herein. In one embodiment the instructions describe oral administration of the construct to a subject. The instructions may alternatively or additionally describe an appropriate dosage regimen, for example any dosage regimen described herein.

In one embodiment a kit comprises one or more further therapeutic(s) described herein.

The construct of the invention may be formulated in any suitable manner and is preferably formulated to facilitate oral administration.

In one embodiment a construct of the invention is in a solid form. Solid forms may include wet or dry powders or granular forms. Powdered forms may include tablets, capsules or pastes.

The construct may be used as a dried powder (e.g. the dried powder is administered to a subject).

In another embodiment, a construct of the invention is formulated as a liquid, suitably wherein the construct is suspended in, or admixed with, a liquid carrier. Said liquid carrier may be water, milk or any other beverage.

In one embodiment the construct may be formulated as part of a foodstuff. Thus, in one aspect the invention provides a foodstuff comprising a construct of the present invention and a foodstuff ingredient. The uses described herein may comprise administering a foodstuff comprising a construct to a subject.

The term "foodstuff" as used herein encompasses "food" for human consumption, as well as "feed" for animal consumption. Preferably a foodstuff is food for human consumption.

Likewise the term "foodstuff ingredient" encompasses both a "food ingredient" for human consumption and a "feed ingredient" for animal consumption.

The foodstuff may be a meat, cereal, or dairy foodstuff. The foodstuff may also be a beverage, such as a juice.

The foodstuff may be a dried foodstuff. In one embodiment the foodstuff has a moisture content of less than 15%, such as less than 12%. Preferably the moisture content is less than 9%.

A meat based foodstuff may comprise non-meat ingredients such as water, salt, flour, milk protein, vegetable protein, starch, hydrolysed protein, phosphate, acid, spices, colouring agents and/or texturising agents. A meat based foodstuff may comprise between 5-99% (weight/weight) meat. In some embodiments the meat based foodstuff may comprise at least 30% (weight/weight) meat, such as at least 50%, at least 60% or at least 70% meat.

The meat based pet food product may include one or more of the following: unprocessed cooked or uncooked meat; dry or semi-dry meats (including cured meats); processed meat products such as emulsified meat products; or ground and/or restructured fresh meat; or retorted products (e.g. autoclaved meat products).

In a preferred embodiment a meat based foodstuff comprises a cooked meat. Preferably a meat based foodstuff is a liver product (e.g. an ox liver product), such as a cooked liver product.

A cereal based foodstuff may include grains, such as corn, rice, wheat, oats, sorghum, barley, rye and/or derivatives thereof. Preferably a cereal based foodstuff is a biscuit.

A dairy foodstuff may be selected from yogurt, cheese or milk. Such foodstuffs may include or be derived from milk from mammals, specifically cows, horses, donkeys, goats, sheep, camels or llamas.

The foodstuff may be a pet food, such as a semi-moist pet food, e.g. kibble form or other forms of pet food, or pet treats.

A pharmaceutical composition or foodstuff may comprise between about 1% to 99% by weight of a construct described herein. Suitably a pharmaceutical composition or foodstuff may comprise between about 5% to 50% or 10% to 40% by weight of a construct described herein. Preferably a pharmaceutical composition or foodstuff may comprise between about 10% to 30% by weight of a construct described herein.

In some embodiments a foodstuff of the invention (e.g. feed) further comprises one or more ingredients selected from: vitamins, proteins, lipids, and carbohydrates. The specific composition of the foodstuff may be formulated specifically for the type/identity of the subject to which the foodstuff will be administered, e.g. based on species.

In one embodiment a construct described herein may be considered to be a prebiotic. Therefore, a construct described herein may have a prebiotic effect on the microbiota (e.g. gut flora, such as the buccal flora) of a subject administered said construct.

The term "prebiotic" as used herein refers to a substrate that is selectively utilised by host microorganisms conferring a health benefit. Thus, a construct described herein may be selectively utilised by the microbiota of a subject, thereby conferring a health benefit.

Prebiotics are extensively discussed in Gibson et al (2017), Nature Reviews Gastroenterology & Hepatology, 14, 491-502, the teaching of which is incorporated herein by reference in its entirety.

In one aspect the invention provides a pharmaceutical composition comprising a construct described herein and a pharmaceutically acceptable carrier. The pharmaceutically acceptable carrier is preferably a liquid carrier, more preferably an aqueous liquid carrier. In preparing such a pharmaceutical composition, the construct may be suspended in, or admixed with, the liquid carrier, and sterilised for example by filtration through a sterile filter using aseptic techniques before transferring to a suitable container. Advantageously additives such as buffering, solubilising, stabilising, preservative or bactericidal or suspending agents may be dissolved in the carrier.

The invention also provides methods for manufacturing a construct described herein, as well as constructs obtainable by a method described herein.

In one aspect a method for manufacturing a construct described herein comprises:
  a. admixing a fatty acid composition and a carrier particle under agitation to provide a homogeneous suspension, wherein the fatty acid composition comprises a C13 to C27 fatty acid, and wherein the carrier particle comprises a hydrophobic region;
  b. admixing water with said homogeneous suspension under agitation to facilitate non-covalent binding of the C13 to C27 fatty acid to a hydrophobic region of the carrier particle; and
  c. isolating said construct.

The term "admix" as used herein means the mixing of at least one constituent with one or more further constituent(s). The term "admix" as used herein refers to mixing constituents in any order, including mixing sequentially or simultaneously. Suitably the term "admix" may refer to the sequential mixing of constituents. The mixture comprising at least one constituent and one or more further constituent(s) may be referred to herein as an "admixture".

All embodiments and descriptions related to the construct and components thereof apply equally to the method of manufacture.

The inventors have found that by admixing a fatty acid composition and carrier particle under agitation in the absence of water the carrier particle can be homogeneously suspended in the composition.

In one embodiment the concentration of carrier particle to fatty acid composition is at least 10, 20, 30, 40, 50, 60, 70, 80, 90 or 100 g/L. For example, the concentration of carrier particle to fatty acid composition may be between about 20 to about 100 g/L, preferably between about 40 to about 80 g/L.

The fatty acid composition may be from any source, and may be natural or synthetic. In one embodiment the fatty acid composition is obtainable from a plant or an animal source.

The fatty acid composition is preferably from a plant, for example from a vegetable, nut, or seed of a plant. The fatty acid composition is preferably an oil. In one embodiment the fatty acid composition is a rapeseed, coconut, cottonseed, castor oil, corn, olive, palm, peanut, safflower, sesame, soybean, sunflower, almond, beech nut, brazil nut, cashew, hazelnut, macadamia, mongongo nut, pecan, pine nut, pistachio, walnut, pumpkin seed, flaxseed, cocoa, or hemp fatty acid composition. In a particularly preferred embodiment the fatty acid composition is a rapeseed fatty acid composition.

Agitation can be effected by any known means (e.g. whisking, blending, or stirring), whether mechanical or otherwise. It is however preferable that the agitation imparts a shearing force upon the admixture. Preferably, the agitation of method step a. and/or b. is achieved by whisking.

The method comprises admixing water with said homogeneous suspension under agitation. The present inventors have found that this advantageously facilitates non-covalent binding of the C13 to C27 fatty acid to a hydrophobic region of the carrier particle, for example by promoting hydrophobic interactions between the carrier particles and fatty acids. Manufacture of the construct of the invention is, therefore, suitably reliant on a thermodynamic association between the fatty acids and hydrophobic region of the carrier particle driven by the presence of water in the admixture (rather than removal of a solvent, for example). Advantageously, the invention provides a simple and efficient method of manufacture, which avoids the need for harsh non-aqueous solvents (e.g. chloroform or methanol). Thus, in one embodiment a method of the invention does not comprise the use of a non-aqueous solvent. In another embodiment a method of the invention does not include a precipitation step.

Admixing water may initially result in the formation of an oil in water or water in oil emulsion. The water is preferably admixed in a stepwise manner until the reaction mixture reaches a suitable viscosity (e.g. where the emulsion is disrupted) allowing separation of the reaction mixture into distinct layers. In one embodiment the ratio of water to oil is at least about 0.7:1 v/v, such as at least about 1:1 or 2:1. In one embodiment the ratio of water to oil is at least about 3:1 or 4:1 v/v. The ratio of water to oil may be between about 0.7:1 v/v to about 2:1 v/v.

Typically, the reaction mixture will separate into three distinct layers, an upper oil layer, a middle aqueous layer comprising the admixed water, and a lower layer comprising the construct of the invention. Separation may be achieved simply by allowing a suitable time period to elapse, however the skilled person will appreciate that separation may be assisted by other techniques known in the art, such as by application of centrifugal force. In one embodiment said time period may be at least 1, 2, 3, 4, 5, 6, 7, 8, 9, 10, 11, 12, 13, 14, 15, 16, 17, 18, 19, 20, 21, 22, 23 or 24 hours. Suitably, said time period may be at least 5 or at least 7 hours, preferably at least 10 or 15 hours. For example, the time period may be at between 5 and 48 hours, such as between 7 and 24 hours.

In one embodiment the construct of the invention is isolated from the reaction mixture by removal of the aqueous and oil layers. Suitably the oil layer may be recycled, thus minimising waste and improving manufacturing economy.

The construct isolated in method step c. may be subjected to further treatments. In one embodiment the construct is dried. Any suitable method may be used, however in one embodiment the construct is heated (e.g. in an oven). In one embodiment the construct is heated at about 50° C. to about 250° C., preferably at about 90° C. to about 150° C. The construct may be heated for at least 1, 2 or 4 hours. Suitably, the construct may be heated between 1 to about 12 hours, such as between about 3 to about 10 hours.

The method may further comprise a granulation step in which the construct is converted into a powdered form (e.g. micronised form). Granulation may be achieved by blending or grinding the construct. Thus, in one embodiment the construct is provided as a micronised powder.

The methods of the invention may further comprise a formulation step in which the construct is admixed with one or more carriers, excipients or foodstuff ingredients. The construct (optionally admixed with one or more carriers or excipients) may be subsequently packaged. For example, the isolated construct may be suspended in a fatty acid composition thereby providing a composition formulated for application to the buccal cavity as described herein. A composition obtainable by said method is also encompassed by the present invention.

Embodiments described herein in respect of the construct per se are intended to be applied equally to the therapeutic uses or methods, or the methods of manufacturing described herein and vice versa.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. The headings provided herein are not limitations of the various aspects or embodiments of this disclosure.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a construct" includes a plurality of such candidate agents and reference to "the fatty acid" includes reference to one or more fatty acids and equivalents thereof known to those skilled in the art.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

EXAMPLES

Example 1

Figure 1:
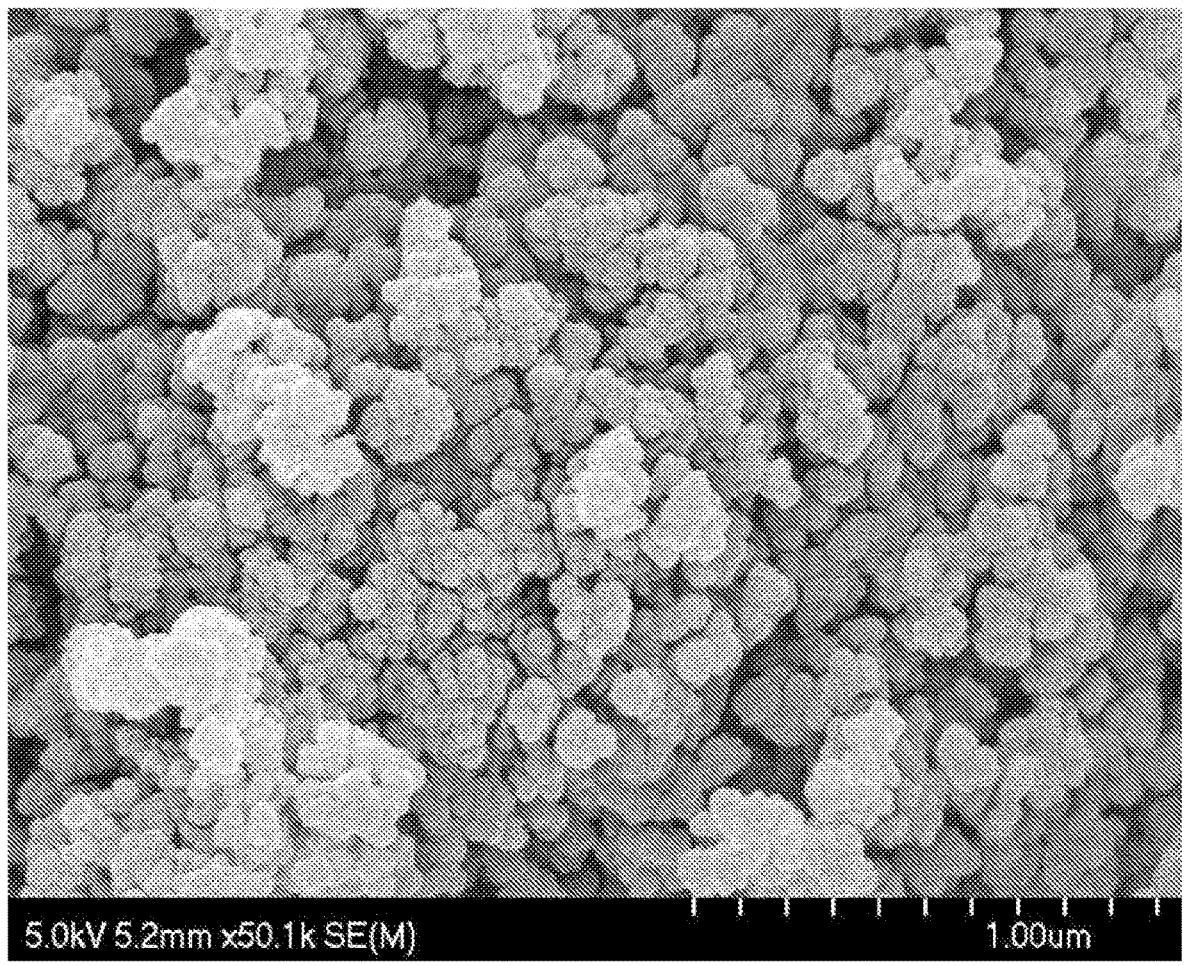
FIG. 1 shows a scanning electron microscopy (SEM) image of the construct of the invention.
Figure 2:
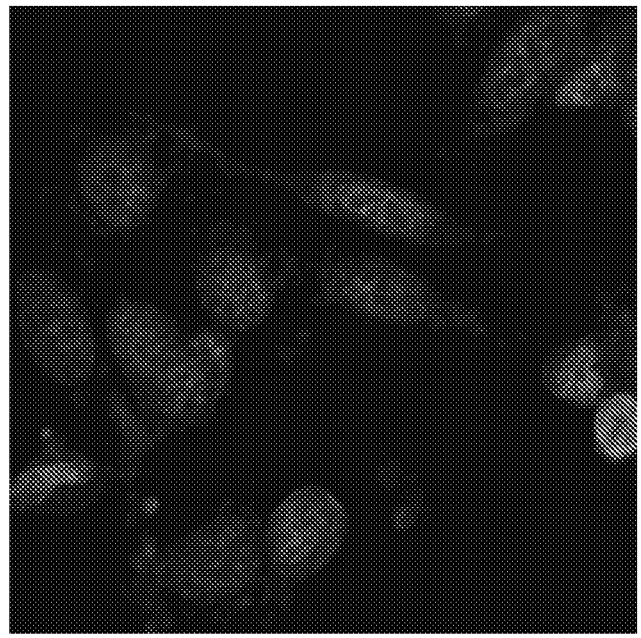
FIG. 2 shows the expression of β-catenin (red) and the position of the nucleus (blue—centre of cells) in (A) control untreated cells (B) Wnt treated (C) Wnt+Construct. The data show an increase in staining for β-catenin in (C) when compared to (A) and (B). Cf. the increase in signal in (C) (301=whole cell, 302=nucleus) when compared to the signal in (B) (201=whole cell, 202=nucleus), and (A) (101=whole cell, 102=nucleus).
Figure 2:
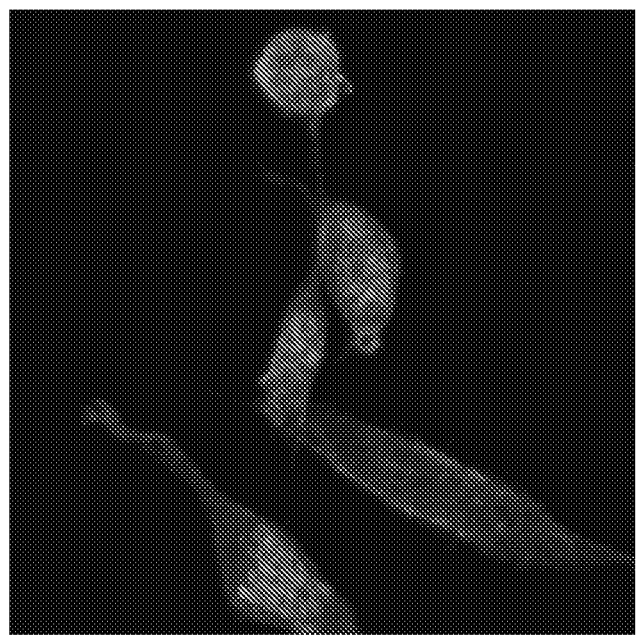
Figure 2:
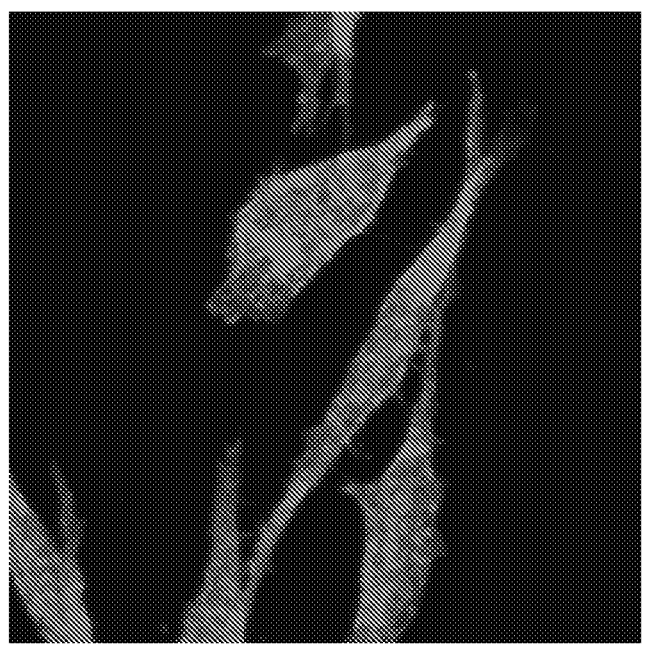

Preparation of the Construct 54 g of pharmaceutical grade silica particles (average diameter ~3.5 µm) were mixed with 1 L of rapeseed oil at room temperature and whisked to avoid clumping of the silica particles and obtain an evenly dispersed homogeneous mixture.

Water was slowly added to a final volume of 2 L (1:1 v/v oil to water ratio). The admixture was left overnight to separate into three layers: a silica particle layer containing constructs comprising fatty acid non-covalently bound to the silica particles; an oil layer; and a water layer. The oil and water layers were removed and the oil recycled. The silica particle layer containing the construct of the invention was baked in an oven at 110° C. for 6 hours and blended to a fine powder.

Example 2

Scanning Electron Microscopy of the Construct

The construct was applied to conductive carbon tape on an aluminium SEM stub and then coated to 0.8 nm thickness using an Agar High Resolution Sputter Coater using a platinum/palladium target and imaged with a Hitachi S-4700 FESEM scanning electron microscope. FIG. 1 shows that the construct forms uniform particles.

Example 3

Constituents of the Construct 10 mg of construct was added to 100 ml of sterile water, and a culture of active *Schistosome cercaria* cells added. The cells were observed under a microscope for 1 hour during which the majority of the *Schistosome cercaria* lost their flagellae. This was in stark contrast to a control (no construct added) in which after the same time period the majority of *Schistosome cercaria* cells retained their flagellae.

Deflagellation occurs when motile cercaria come in contact with the linoleic acid on human skin and is a precursor to the deflagellate cercaria burrowing through the skin into the body of the host in order to complete their life cycle.

The results of this experiment validate the presence of fatty acids bound to the silica particles, and in particular demonstrate the presence of linoleic acid bound to the silica particles.

Example 4

Intracellular Release and Migration of β-Catenin

Cells of a prostate cancer cell line (PC3) were exposed to the construct (suspended in phosphate buffered saline at 0.01 g/ml) or a $SiO_2$ control for 25 minutes with or without Wnt (100 ng/ml) in a chamber slide. The cells were washed after treatment and fixed in 4% formalin for 30 minutes at 4° C. Cells were washed 3 times with ice-cold PBS and stored in 0.5 ml of PBS at 4° C. for immunostaining.

For immunostaining, cells were washed twice for 5 minutes in a Tris base buffer (TB) containing 20 mM Tris, pH 7.4, 0.9% NaCl, 0.1% Tween 20. Cells were then incubated in 20% normal goat serum/TB for 30 minutes at room temperature, the chambers were drained, and cells were incubated with mouse anti-β-catenin (ab22656, Abcam) overnight at 4° C. Following two washes in TB, cells were incubated in goat anti-mouse peroxidase Fab (Abcam). Following a further two 5-minute washes in TBST, cells were incubated with tyramide Cy3 for 10 minutes at room temperature. Cells were washed twice for 5 minutes in TBST before nuclear counterstaining with DAPI. After a final two 5-minute washes, a coverslip was placed on the slides.

Fluorescence immunocytochemical staining for β-catenin expression in cell lines was visualized using a confocal inverted microscope using a 20×0.7 numerical aperture or 40×1.0 numerical aperture dry objective. DAPI (nuclear counterstain) was excited at 405 nm with an emission of 415-500 nm; Cy3 (β-catenin-labeled) signal was excited at 561 nm with an emission spectrum between 570-670 nm. Laser power, gain, and off-set settings for the photomultiplier tubes were kept similar for comparable samples.

The results show the expression of β-catenin (red) and the position of the nucleus (blue) in (A) control untreated cells (B) Wnt treated (C) Wnt+Construct. The data demonstrate an increase in the translocation of β-catenin in the cells treated with the construct of the invention.

In conclusion, these data indicate that the constructs of the invention are pharmaceutically active. Moreover, the Wnt signalling pathway has been implicated in behaviour, with dysfunctional Wnt signalling aberrantly regulating new neurone development and cognitive function. Indeed many conventional mood stabilisers mediate their effect via modulation of Wnt signalling. Specifically, it has been found that rats treated with the mood stabilisers, lithium and valproate, show increased levels of β-catenin, which is indicative of an activation of the Wnt pathway. Likewise, a number of antipsychotics (e.g. Haloperidol, and Risperidone) and antidepressants (e.g. Fluoxetine, Fluvoxamine, and Venlafaxine) have been determined to increase Wnt/β-catenin signalling. Therefore the benefits of the construct in improving behaviour may (at least in part) be achieved by modulating Wnt/β-catenin signalling.

Example 5 c-Fos Expression

Dose of Construct

Animals are dosed based on weight. The concentration of construct used is 33.33 mg/kg (a 750 kg horse receives a dose of 25 g), e.g. for a 300 g rat: 0.3 kg×33.33 mg=9.999 mg (10 mg). The construct is ground into a fine powder and solubilised in $ddH_2O$ with the aid of a water bath sonicator. The construct is frozen at −20° C., and thawed prior to gavage.

Protocol

Non-recovery anaesthesia is induced with inhalation of isoflurane followed by IP injection of sodium pentobarbital. An IV cannula is inserted (maintenance doses of anaesthesia are administered through IV cannula). A tracheotomy is performed and a feeding tube inserted, which is followed by a 2-hour recovery period.

The construct is administered by gavage (in 5 ml ddH$_2$O) via feeding tube followed by a 1-hour recovery period.

Perfusion fixation is carried out (4% PFA), brains removed and incubated in post-fix solution then 30% sucrose solution. The brains are flash frozen and sectioned at 44 μm on a freezing microtome. The free-floating sections are subjected to fos immunohistochemistry.

The same protocol is followed for control animals, except that no substance is gavaged.

Fos+ Nuclei Counts

The results show a significant increase in Fos+ nuclei/section in the paraventricular nucleus of rats administered the construct when compared to control rats.

Example 6

Treatment of Oestrus-Associated Behaviour

Three adult mares with behavioural problems associated with ovulation were administered 5 g of the construct with their evening feed on the day that it was evident that they were in the oestrus phase of the oestrous cycle.

A veterinary-gauged semi-quantitative clinical scoring system was adopted to assess behaviour:
1=normal good behaviour;
2=mildly bad behaviour;
3=moderately bad behaviour;
4=severely bad behaviour; and
5=very severe bad behaviour with significant and often dangerous handling/management problems.

Bad behaviour was characterised by a wide range of clinical signs, including squirting, kicking, biting, squealing, aggression, grumpiness, bucking, being easily spooked, anxiety, neighing when ridden, wind sucking, weaving, frequent urination, difficulty catching, tacking-up, loading and riding outside the stables, and poor performance.

Prior to administration of the construct the behavioural scores were 4.5 indicating behaviour creating severe management problems. The next morning all three animals were behaving normally with behavioural scores of 1.5, thus demonstrating a stark and reproducible improvement in behaviour following administration of a construct of the invention.

Example 7

Modulation of Pituitary Gland Activity

A human subject is administered 1 g of the construct formulated as part of a yogurt product. Blood samples are taken prior to administration of the construct and 1, 2, 5, and 10 hours after administration, plasma is isolated and subjected to mass spectrometry. The mass spectrometry data show increased secretion of pituitary gland hormones, including oxytocin and ACTH, associated with administration of the construct.

Example 8

Treatment of Rheumatoid Arthritis

A patient diagnosed with rheumatoid arthritis is administered with 1 g of the construct daily, and a change in symptoms (such as: joint pain and swelling; stiffness; fatigue; depression; irritability; anaemia; and flu-like symptoms) monitored. After 1 week of treatment the symptoms are vastly reduced/eliminated, in particular, the patient has improved mobility and reduced pain.

Example 9

Treatment of Periodontal Disorders

A construct manufactured as per Example 1 was formulated as a toothpaste for application to the teeth and gums. The toothpaste was prepared by the addition of rapeseed oil to a finely ground powdered form of the construct with stirring at 22° C. The rapeseed oil was added in excess until a paste of appropriate density was formed. The paste was then loaded into flexible tubes which were subsequently sealed.

To assess gum health, pocket depth was measured using a probe in accordance with routine dental hygiene techniques. Two human subjects were instructed to brush once daily in the evening either instead of using standard toothpaste or after such use with vigorous washing to remove any residual standard toothpaste for 2 minutes with the toothpaste formulation comprising the construct for a period of at least 4 weeks. Pocket depth was measured before and after the period of 4 weeks, and results are presented in the table below:

| Subject | Pre-Treatment Worst Pocket Depth (mm) | Post-Treatment Pocket Depth (mm) |
|---------|---------------------------------------|----------------------------------|
| 1 | 5 | 0 |
| 2 | 8 | 2 |

Hence, it was concluded that the toothpaste comprising the construct reduced the pocket depth, thus improving gum health and providing a treatment for periodontal disorders.

Example 10

Largescale Periodontal Treatment Trial

Twenty patients in Sydney, Australia and 10 patients in Szeged, Hungary, are selected for participation in this trial. Full periodontal charting is carried out for each patient prior to treatment to indicate the state of health of the bone and gums around each tooth. The patients are given instructions on how to use the toothpaste of Example 9, and after a period of time (a maximum of 30 days) their gum health is re-examined. The examination consists of the measurement of pocket depth, the measurement of the cemento enamel junction to the gingival margin and bleeding of the gums with probing, each of which is improved following use of the toothpaste of the invention.

Example 11

Treatment of Bowel Inflammation

An experiment is set up to explore the inflammation in the bowel of rats post introduction of trinitrobenzenesulphonic acid transanally to the colon. This agent causes an acute inflammation peaking at three days after introduction of the irritant. Tissue levels of tumour necrosis factor, the histopathological changes, and the gut flora at the site of inflammation are measured. These parameters of response are assessed in rats given ten day in advance feed containing the construct of the invention and a control feed with no product incorporated.

Experimental Procedure

Male rats are used: ~240 g (n=10-12/group).

Day 0—Colonic instillation of trinitrobenzene sulphonic acid (TNBS; 10 mg).

Day 3—Removal of distal colon (8 cm), opened longitudinally, washed.

Evaluation of colonic damage using stereomicroscope and computerized planimetry.

Determination of myeloperoxidase activity and other biomarkers including TNF.

Primary Endpoints:

Area of Colonic Damage.

Macroscopic Colitis Damage Score.

Myeloperoxidase activity (MPO-index of neutrophil infiltration).

Food weights (commencing Day—11 i.e. 24 h prior to challenge).

Measurement of colonic tissue TNF-alpha (for all animals in all groups).

Measurement of colonic tissue IL-B (for all animals in all groups).

Secondary Endpoints:

Colonic segment weight (index of tissue oedema).

Daily body weight.

The feed containing the construct of the invention is found to reduce the induced inflammation and all parameters thereof.

Example 12

Modulation of Equine Microbiota

Phase 1

In vitro analysis is performed of the effects of direct application of a construct of the invention to metabolic parameters of equine gut microbiota including gas production and production of low weight fatty acids with the necessary controls.

Phase 2

The array of bacteria in the gut microbiota of ten horses is analysed twice during a period of a fortnight followed by administration of feed comprising a construct of the invention or a control feed lacking said construct. Weekly observations on the gut microbiota during the following three weeks is performed.

The results demonstrate that a construct of the invention has a significant effect on the gut microbiota of the fed animals, and thus supports the classification of the construct as a prebiotic.

Example 13

Anxiolytic Properties of the Constructs

Study 1

A study is performed on horses confined in a university hospital setting prior to their confinement for the induction of anaesthesia, which is a stressor for horses. Both behavioural and cardiac rate measurements are taken for horses administered the construct and those administered a control (lacking the construct).

The results demonstrate that the construct has a significant anxiolytic effect.

Study 2

A study is performed using horses that have been discharged from a university hospital with the recommendation of box rest. Such confinement is problematic, as it causes anxiety for the horses, leading to owner non-compliance of this veterinary recommendation. Behavioural and cardiac measurements are taken for horses administered the construct and those administered a control (lacking the construct).

The results demonstrate that the construct calms the horses during the confinement period, leading to improved owner compliance with regard to the box rest.

Example 14

Treatment of Oral Disorders

The toothpaste manufactured in accordance with Example 9 was provided to two dental practices for the evaluation of efficacy.

One of the dental practices that works solely with implants gave the paste to patients after putting in the implants and reported better healing rates, as measured by the dentist.

In another practice, patients suffering from chronic gingivitis showed significant improvements, in that their gum pockets started to return to normal. Moreover, two elderly women suffering from chronic gingivitis also showed significant improvement in their gum health.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for treating a disorder selected from the group consisting of inflammatory bowel disease (IBD), ulcerative colitis, and Crohn's disease, the method comprising:

administering to a subject in need thereof an effective amount of a construct obtained by a method comprising:

admixing a fatty acid composition and a non-biological and non-biodegradable carrier particle under agitation to provide a homogeneous suspension, wherein the fatty acid composition comprises a C13 to C27 fatty acid, and wherein the non-biological and non-biodegradable carrier particle comprises a hydrophobic region;

admixing water with said homogeneous suspension under agitation to facilitate non-covalent binding of an aliphatic chain of the C13 to C27 fatty acid to the hydrophobic region of the non-biological and non-biodegradable carrier particle; and removing excess water and excess fatty acid thereby treating said disorder.

2. The method of claim 1, wherein the C13 to C27 fatty acid comprises a C14 to C26 fatty acid or a C17 to C19 fatty acid selected from a linoleic acid, a palmitic acid, a stearic acid, an oleic acid, and/or a linolenic acid;

the non-biological and non-biodegradable carrier particle is a silica particle having an average diameter of about 3.5 µm; and the construct is administered to the subject as part of a foodstuff.

3. The method of claim 1, wherein the C13 to C27 fatty acid comprises a C14 to C26 fatty acid or a C17 to C19 fatty acid.

4. The method of claim 1, wherein the C13 to C27 fatty acid comprises a linoleic acid, a palmitic acid, a stearic acid, an oleic acid, and/or a linolenic acid.

5. The method of claim 1, wherein the non-biological and non-biodegradable carrier particle is a silica particle, a kaolin particle, or a vermiculite particle.

6. The method of claim 1, wherein the non-biological and non-biodegradable carrier particle has an average diameter of about 1.0 μm to about 10.0 μm.

7. The method of claim 1, wherein the construct is administered to the subject as part of a foodstuff.

8. The method of claim 7, wherein the construct does not cross a mucosal layer of a gastrointestinal tract of the subject.

9. The method of claim 1, wherein the subject is a human, an equine, a canine, a bovine, a porcine, an ovine, a caprine, a feline, a chicken, a rodent, a fish, or a camelid.

10. The method of claim 1, wherein the treating modulates the subject's microbiota.

11. The method of claim 1, wherein the treating modulates the subject's buccal flora.

12. The method of claim 1, wherein the treating alters a composition of the subject's microbiota.

13. The method of claim 1, wherein the treating increases permeability of the subject's gut to bacterial vesicles or microvesicles.

14. The method of claim 1, wherein the treating increases permeability of the subject's gut to food, microbiota or components thereof.

15. The method of claim 1, wherein the treating modulates the subject's hypothalamus-pituitary-adrenal (HPA) axis.

16. The method of claim 1, wherein the disorder is IBD.

17. The method of claim 1, wherein the disorder is ulcerative colitis.

18. The method of claim 1, wherein the disorder is Crohn's disease.

19. The method of claim 1, wherein all excess water and all excess fatty acid is removed.

20. A method for manufacturing a construct for oral administration comprising:
   admixing a fatty acid composition and a non-biological and non-biodegradable carrier particle under agitation to provide a homogeneous suspension, wherein the fatty acid composition comprises a C13 to C27 fatty acid, and wherein the non-biological and non-biodegradable carrier particle comprises a hydrophobic region;
   admixing water with said homogeneous suspension under agitation to facilitate non-covalent binding of an aliphatic chain of the C13 to C27 fatty acid to the hydrophobic region of the non-biological and non-biodegradable carrier particle; and
   removing excess water and excess fatty acid.

21. The method of claim 20, wherein all excess water and all excess fatty acid is removed.

22. A method for treating a disorder, the method comprising:
   administering to a subject a construct, the construct obtained by a method comprising:
      admixing a fatty acid composition and a non-biological and non-biodegradable carrier particle under agitation to provide a homogeneous suspension, wherein the fatty acid composition comprises a C13 to C27 fatty acid, and wherein the non-biological and non-biodegradable carrier particle comprises a hydrophobic region;
      admixing water with said homogeneous suspension under agitation to facilitate non-covalent binding of an aliphatic chain of the C13 to C27 fatty acid to the hydrophobic region of the non-biological and non-biodegradable carrier particle; and
      removing excess water and excess fatty acid;
   thereby treating the disorder.

23. The method of claim 22, wherein all excess water and all excess fatty acid is removed.

* * * * *